(12) United States Patent
Truckai et al.

(10) Patent No.: US 11,096,560 B2
(45) Date of Patent: Aug. 24, 2021

(54) ENDOSCOPE WITH MULTIPLE IMAGE SENSORS

(71) Applicant: Meditrina, Inc., Cupertino, CA (US)

(72) Inventors: Csaba Truckai, Saratoga, CA (US); Daniel Truckai, Saratoga, CA (US); Khoi Le, San Jose, CA (US); Kevin Moss, Tracy, CA (US); Nicholas Landgraf, Huntington Woods, MI (US); Britta Nelson, Loomis, CA (US)

(73) Assignee: Meditrina, Inc., Cupertino, CA (US)

( * ) Notice: Subject to any disclaimer, the term of this patent is extended or adjusted under 35 U.S.C. 154(b) by 457 days.

(21) Appl. No.: 15/712,603

(22) Filed: Sep. 22, 2017

(65) Prior Publication Data

US 2018/0084971 A1    Mar. 29, 2018

Related U.S. Application Data

(60) Provisional application No. 62/399,193, filed on Sep. 23, 2016, provisional application No. 62/399,204, filed on Sep. 23, 2016.

(51) Int. Cl.
*A61B 1/00* (2006.01)
*A61B 1/05* (2006.01)
(Continued)

(52) U.S. Cl.
CPC ...... *A61B 1/00135* (2013.01); *A61B 1/00082* (2013.01); *A61B 1/00096* (2013.01);
(Continued)

(58) Field of Classification Search
CPC .......... A61B 1/00082; A61B 1/00096; A61B 1/00135; A61B 1/00174; A61B 1/00179;
(Continued)

(56) References Cited

U.S. PATENT DOCUMENTS

| 218,055 A | 7/1879 | Nitze |
|---|---|---|
| 879,224 A | 2/1908 | Wappler |

(Continued)

FOREIGN PATENT DOCUMENTS

| EP | 1985226 A2 | 10/2008 |
|---|---|---|
| WO | WO-2016079141 A1 | 5/2016 |

(Continued)

OTHER PUBLICATIONS

Co-pending U.S. Appl. No. 15/836,460, filed Dec. 8, 2017.
(Continued)

*Primary Examiner* — Aaron B Fairchild
(74) *Attorney, Agent, or Firm* — Wilson Sonsini Goodrich & Rosati

(57) ABSTRACT

A disposable cover for use with an endoscope includes an elongated sheath having and having an open proximal end and a closed distal end. A channel extends along a central axis of the sheath from the open proximal end to the closed distal end, and the channel is configured to accommodate insertion of an endoscope. A proximal region of the sheath is formed as a rigid thin-wall sleeve and a distal region of the sheath is formed as a flexible thin-wall sleeve. The flexible thin-wall sleeve is configured to allow deflection of said distal region in cooperation with an articulating distal end of an endoscope.

18 Claims, 17 Drawing Sheets

(51) Int. Cl.
  *G02B 23/24* (2006.01)
  *G02B 15/10* (2006.01)
  *A61B 1/06* (2006.01)
  *A61B 1/005* (2006.01)

(52) U.S. Cl.
  CPC ...... *A61B 1/00105* (2013.01); *A61B 1/00142* (2013.01); *A61B 1/00174* (2013.01); *A61B 1/00179* (2013.01); *A61B 1/00181* (2013.01); *A61B 1/0051* (2013.01); *A61B 1/00087* (2013.01); *A61B 1/00165* (2013.01); *A61B 1/05* (2013.01); *A61B 1/0676* (2013.01); *G02B 15/10* (2013.01); *G02B 23/2407* (2013.01)

(58) Field of Classification Search
  CPC . A61B 1/00181; A61B 1/00142; A61B 1/005; A61B 1/0051; A61B 1/0052; A61B 1/0053; A61B 1/0055–58; A61B 1/008; A61B 1/00154; A61B 1/0142
  See application file for complete search history.

(56) References Cited

U.S. PATENT DOCUMENTS

| | | | |
|---|---|---|---|
| 1,021,810 A | 4/1912 | Wappler et al. | |
| 1,303,135 A | 5/1919 | Wappler | |
| 1,627,941 A | 5/1927 | Wappler | |
| 1,712,866 A | 5/1929 | Noah et al. | |
| 1,958,656 A | 5/1934 | Leo et al. | |
| 3,496,930 A | 2/1970 | Wappler et al. | |
| 3,908,637 A | 9/1975 | Doroshow | |
| 4,024,869 A | 5/1977 | Bonnet | |
| 4,402,310 A | 9/1983 | Kimura | |
| 4,423,727 A | 1/1984 | Widran et al. | |
| 5,025,778 A | 6/1991 | Silverstein et al. | |
| 5,191,878 A | 3/1993 | Iida et al. | |
| 5,483,951 A * | 1/1996 | Frassica | A61B 1/00142 600/104 |
| 5,554,098 A * | 9/1996 | Yabe | A61B 1/00137 600/121 |
| 5,573,493 A * | 11/1996 | Sauer | A61B 1/00101 600/121 |
| 5,575,756 A * | 11/1996 | Karasawa | A61B 1/00068 600/121 |
| 5,865,621 A * | 2/1999 | Calderwood | A61B 1/00142 433/116 |
| 5,976,075 A | 11/1999 | Beane et al. | |
| 6,066,090 A | 5/2000 | Yoon | |
| 6,086,530 A * | 7/2000 | Mack | A61B 1/00135 600/121 |
| 6,174,307 B1 | 1/2001 | Daniel et al. | |
| 6,452,626 B1 | 9/2002 | Adair et al. | |
| 6,997,896 B2 | 2/2006 | Novak | |
| 8,277,373 B2 | 10/2012 | Maahs et al. | |
| 8,460,182 B2 | 6/2013 | Ouyang et al. | |
| 8,702,594 B2 | 4/2014 | Edidin et al. | |
| 9,468,367 B2 | 10/2016 | Ouyang et al. | |
| 9,901,246 B2 | 2/2018 | Whitmore, III | |
| 9,913,570 B2 | 3/2018 | Kucharski et al. | |
| 10,433,717 B1 | 10/2019 | Truckai et al. | |
| 10,524,636 B2 | 1/2020 | Ouyang et al. | |
| 10,569,060 B2 | 2/2020 | Jenkins et al. | |
| 2002/0161281 A1 * | 10/2002 | Jaffe | A61B 5/065 600/114 |
| 2005/0101838 A1 | 5/2005 | Camillocci et al. | |
| 2005/0197623 A1 | 9/2005 | Leeflang et al. | |
| 2005/0234296 A1 | 10/2005 | Saadat et al. | |
| 2005/0272977 A1 | 12/2005 | Saadat et al. | |
| 2006/0100615 A1 | 5/2006 | McIntyre et al. | |
| 2006/0189845 A1 | 8/2006 | Maahs et al. | |
| 2006/0235458 A1 | 10/2006 | Belson | |
| 2007/0293726 A1 | 12/2007 | Goldfarb et al. | |
| 2008/0108869 A1 | 5/2008 | Sanders et al. | |
| 2008/0154184 A1 | 6/2008 | Blight et al. | |
| 2008/0195128 A1 | 8/2008 | Orbay et al. | |
| 2008/0275483 A1 | 11/2008 | Makower et al. | |
| 2009/0048486 A1 | 2/2009 | Surti | |
| 2009/0082622 A1 | 3/2009 | Takekoshi et al. | |
| 2009/0231419 A1 | 9/2009 | Bayer | |
| 2009/0281388 A1 | 11/2009 | Ito | |
| 2009/0318758 A1 | 12/2009 | Farr et al. | |
| 2009/0318797 A1 | 12/2009 | Hadani | |
| 2010/0217082 A1 | 8/2010 | Ito et al. | |
| 2010/0249510 A1 * | 9/2010 | Yamada | A61B 1/00142 600/121 |
| 2010/0298642 A1 | 11/2010 | Trusty et al. | |
| 2011/0092766 A1 | 4/2011 | Monassevitch et al. | |
| 2011/0130629 A1 * | 6/2011 | Watanabe | A61B 1/00142 600/125 |
| 2011/0152617 A1 | 6/2011 | Iwamizu et al. | |
| 2011/0184233 A1 | 7/2011 | Fructus et al. | |
| 2012/0016191 A1 | 1/2012 | Ito et al. | |
| 2014/0228875 A1 | 8/2014 | Saadat | |
| 2015/0119795 A1 | 4/2015 | Germain et al. | |
| 2016/0174819 A1 | 6/2016 | Ouyang et al. | |
| 2017/0035277 A1 | 2/2017 | Kucharski et al. | |
| 2017/0265879 A1 | 9/2017 | Washburn, II | |
| 2017/0319047 A1 | 11/2017 | Poulsen et al. | |
| 2018/0184892 A1 | 7/2018 | Truckai et al. | |
| 2018/0199797 A1 | 7/2018 | London Brown et al. | |
| 2018/0206712 A1 | 7/2018 | Begg | |
| 2019/0262512 A1 | 8/2019 | Palushi et al. | |

FOREIGN PATENT DOCUMENTS

| | | |
|---|---|---|
| WO | WO-2016138128 A1 | 9/2016 |
| WO | WO-2018111780 A1 | 6/2018 |

OTHER PUBLICATIONS

Co-pending U.S. Appl. No. 15/861,474, filed Jan. 3, 2018.
International Search Report and Written Opinion dated Mar. 6, 2018 for International PCT Patent Application No. PCT/US2017/065635.
Office action dated Apr. 8, 2020 for U.S. Appl. No. 15/826,460.
Office action dated Apr. 17, 2020 for U.S. Appl. No. 15/861,474.
Extended European Search Report dated Jun. 29, 2020 for EP17880946.
Office action dated Sep. 16, 2020 for U.S. Appl. No. 15/836,460.

* cited by examiner

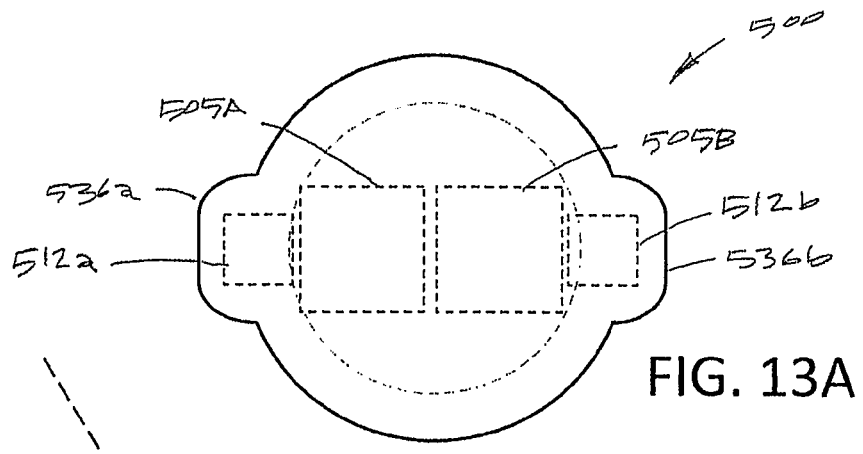
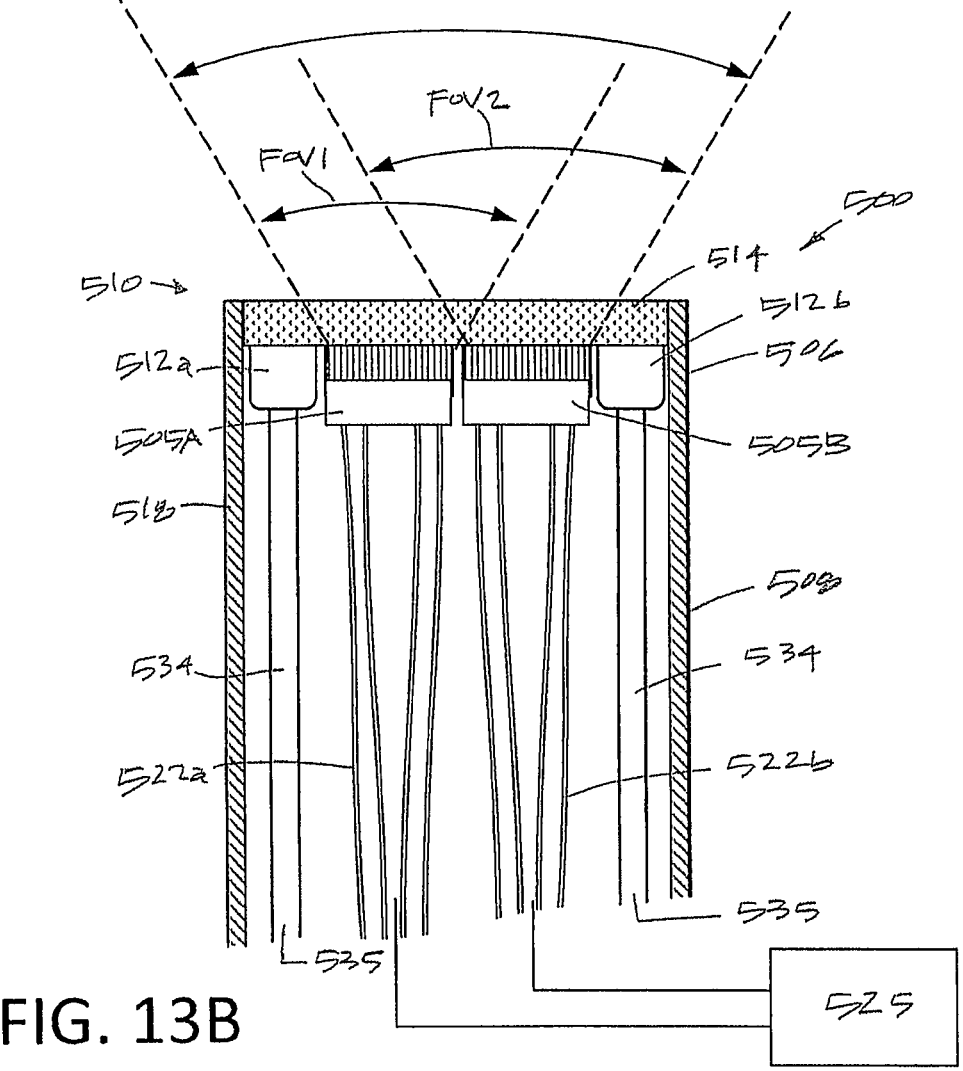
FIG. 13A
FIG. 13B

ENDOSCOPE WITH MULTIPLE IMAGE SENSORS

CROSS-REFERENCE TO RELATED APPLICATIONS

This application claims the benefit of U.S. Provisional Application No. 62/399,193, filed on Sep. 23, 2016, and of U.S. Provisional Application No. 62/399,204, filed on Sep. 23, 2016, each of which is incorporated herein by reference in their entirety.

BACKGROUND OF THE INVENTION

1. Field of the Invention

This invention is directed towards disposable sterile covers or sheaths for use with non-disposable endoscopes. More particularly, it is directed toward a disposable sterile sheath having a flexible or elastomeric working end for cooperating with an articulating distal end of an endoscope.

2. Description of the Background Art

Endoscope covers are described in US2012/0016191; US2011/0152617; US2011/0130629; US2010/0217082; US2009/0281388; and US20050101838.

SUMMARY OF THE INVENTION

In a first aspect of the present invention, a disposable cover for use with an endoscope includes an elongated sheath having and having an open proximal end and a closed distal end. A channel extends along a central axis of the sheath from the open proximal end to the closed distal end, and the channel is configured to accommodate insertion of an endoscope. A proximal region of the sheath is formed as a rigid thin-wall sleeve and a distal region of the sheath is formed as a flexible thin-wall sleeve. The flexible thin-wall sleeve is configured to allow deflection of said distal region in cooperation with an articulating distal end of an endoscope.

In certain embodiments of the disposable cover, the flexible thin-wall sleeve of said distal region may be configured to allow a side-to-side deflection and/or an axial deflection. For example, the flexible thin-wall sleeve of said distal may be deformable in a lateral direction and/or stretchable in an axial direction.

In other embodiments of the disposable cover, the proximal region of the sheath may include a lock mechanism for locking said proximal region to a shaft of the endoscope. In some instances, the lock mechanism may comprise a turn-screw or other clamp mechanism. In other instances, the lock mechanism may include cooperating first and second engagement features on the sheath and endoscope respectively.

In still other embodiments of the disposable cover the closed distal tip of the distal region of the sheath comprises at least one lens. For example, the lens may be adapted modify the field of view of an image sensor or optical waveguide in the endoscope. Alternatively or additionally, the lens may be adapted modify an angle of illumination of a light emitter in the endoscope.

In further embodiment of the disposable cover s, the sheath may have at least a first key feature which cooperates with a second mating key feature on the endoscope to thereby maintain the distal region of the sheath in a predetermined rotational position relative to the endoscope. The first key feature may be disposed in or on the distal region of sheath and may be configured to engage or conform to a feature or shape of a distal end of the endoscope. Alternatively or additionally, the first key feature may be disposed in the proximal region of sheath and may be configured to engage the second mating key feature in a proximal portion of the endoscope.

In further embodiment of the disposable cover, the sheath may have at least a first key feature which cooperates with a second mating key feature on the endoscope to thereby maintain the distal region of the sheath in a predetermined rotational position relative to the endoscope. The first key feature may be disposed in or on the distal region of sheath and may be configured to engage or conform to a feature or shape of a distal end of the endoscope. Alternatively or additionally, the first key feature may be disposed in the proximal region of sheath and may be configured to engage the second mating key feature in a proximal portion of the endoscope.

In yet other embodiments of the disposable cover, the disposable cover may further comprise any one or more of a resilient material for interfacing with a distal surface of an endoscope; an inflation channel in a wall of the sheath communicating with an inflatable balloon carried by a medial region of the sheath; an inflow channel in a wall of the elongated sheath, wherein the inflow channel is adapted for coupling to a fluid source for providing a fluid inflow to the interior of a patient's body; an outflow channel in a wall of the elongated sheath adapted for coupling to a negative pressure source for providing fluid outflow from the interior of a patient's body; at least one working channel in a wall of the sheath extending from an open proximal end to an open distal end for introducing a medical device therethrough; an outflow channel in a wall of the elongated sheath adapted for coupling to a negative pressure source for providing fluid outflow from the interior of a patient's body; at least one working channel in a wall of the sheath extending from an open proximal end to an open distal end for introducing a medical device therethrough; and an inflatable balloon carried by a medial region of the sheath and further having an open end in a distal portion of the sheath for providing a fluid inflow to the interior of a patient's body.

In another aspect of the resent invention, an endoscope comprises an elongated member extending about a central axis and carrying a plurality of image sensors in or over a distal region thereof. Each image sensor has an different field of view, and said differing fields of view have an overlap. An image processor is programmed with imaging processing algorithms that mesh images from each imaging sensor having a different field of view to provide a single seamless image. In specific embodiments, the elongated member carry two, three, four, or more image sensors, and the image sensors may be orthogonally oriented or non-orthogonally angled relative to said central axis. In other embodiments, a prism may be provided for modifying the field of view or each of the image sensors.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13A is an end view of the distal end of an endoscope with two imaging sensors.

FIG. 13B is a longitudinal sectional view of the endoscope distal end of FIG. 13A showing the fields of view of the two imaging sensors.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The disposable cover or sheaths of the present invention include disposable sheaths for use with surgical devices, and are particularly useful in providing sterility for endoscopes as well as providing additional functionality in the form of fluid inflow and outflow channels in a wall of the sheath for cooperating with a fluid management system.

Figure 1:
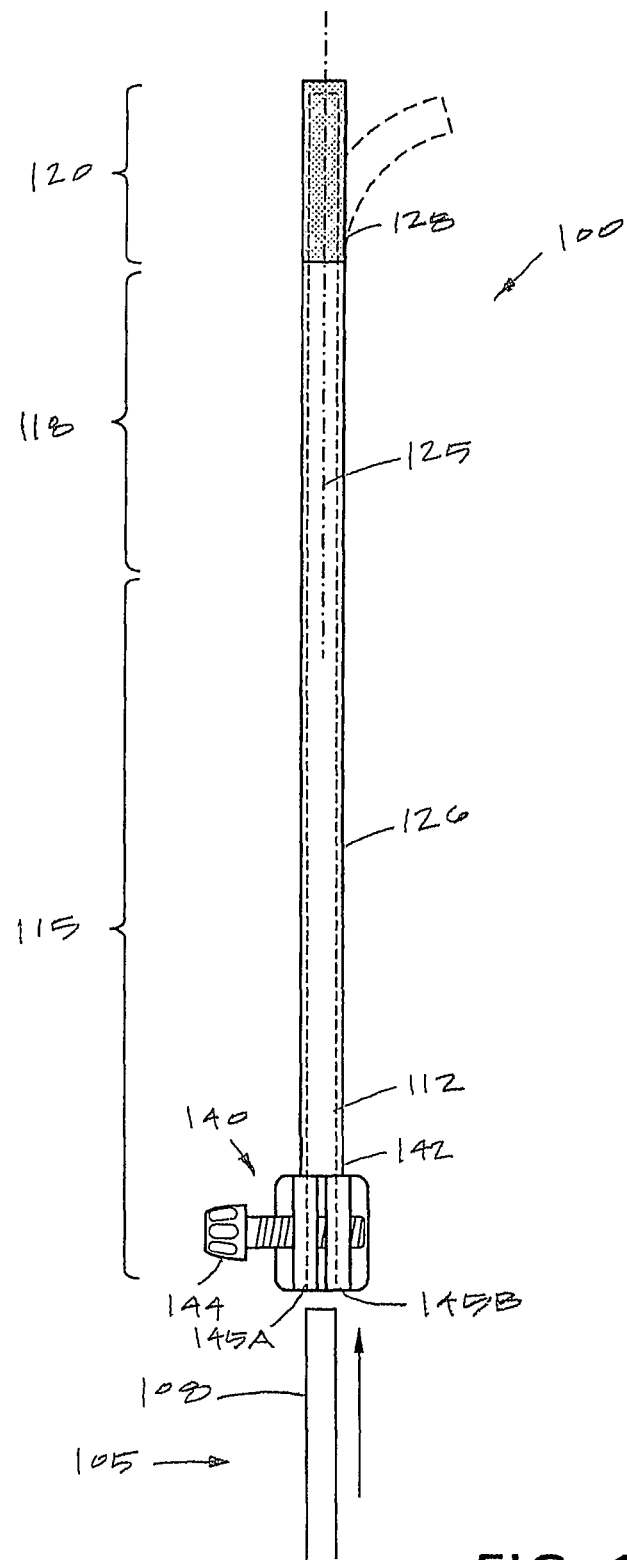
FIG. 1 shows a disposable thin-wall sheath in plain view corresponding to the invention that is adapted to fit over and cover the shaft of an endoscope, the sheath having a distal region that is flexible and axially stretchable to cooperate with an articulating endoscope.

FIG. 1 shows a sheath 100 that is adapted to cover an endoscope 105. The endoscope 105 has an elongate shaft portion 108 that can be inserted into the interior channel 112 of the sheath 100.

In this embodiment, the sheath 100 and the proximal region 115, a medial region 118 and a distal region 120 as shown in FIG. 1. As can be seen in FIG. 1, the sheath 100 extends along a central axis 125 with the proximal region 115 of the sheath consisting of a rigid thin-wall sleeve 126 that can be fabricated of any suitable material, for example, a metal such as stainless steel or an extruded polymer material. As will be described below, a variation of the sheath 100 has at least one lumen or channel in the sheath wall for use as inflow or outflow channels or as a working channel for insertion of a tool therethrough.

Still referring to FIG. 1, the distal region 120 of the sheath 100 can extend over a length of 1 cm to 5 cm, and more often a length of 1 cm to 2 cm, and comprises a sleeve 128 of a thin-wall flexible material. In one variation, the flexible material comprises an elastomer or includes an elastomeric component so that the distal region 120 can flex from side-to-side as well as stretch axially relative to axis 125 for reasons described below.

In FIG. 1, it can be seen that the proximal region 115 of the sheath 100 includes a clamp mechanism 140 for locking the proximal end 142 of sleeve 126 to the endoscope shaft 108. In one variation, the clamp mechanism 140 can comprise a turn-screw 144 configured to squeeze clamp portions 145A and 145B on to the endoscope shaft 108.

Figure 2:
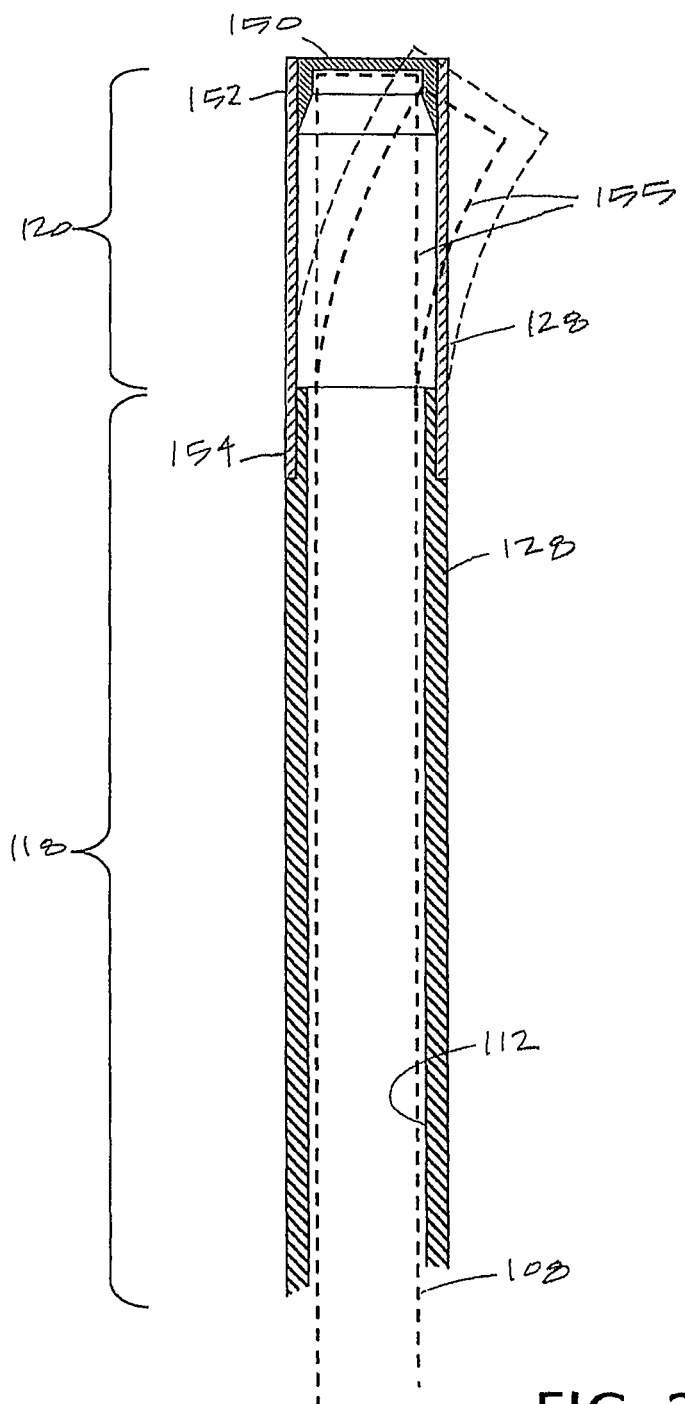
FIG. 2 is an enlarged longitudinal sectional view of the medial and distal regions of the sheath of FIG. 1, illustrating the distal sheath region that is flexible and axially stretchable.

Now turning to FIG. 2, it can be seen that the distal region 120 of the sheath 100 terminates in a distal end cap 150 that closes the end of interior channel 112 that accommodates the endoscope shaft 108. The end cap 150 is of a transparent material such as a plastic or glass to allow viewing therethrough. The end cap 150 can be attached to the distal end 152 of the flexible sleeve 128 of the distal sheath region 120 with adhesives or any other suitable form of fluid-tight bonding. Similarly, the proximal end 154 of the flexible sleeve 128 of distal sheath region 120 can be attached to the rigid sleeve 126 of the proximal region 115 by adhesives or other suitable bonding means.

Figure 3:
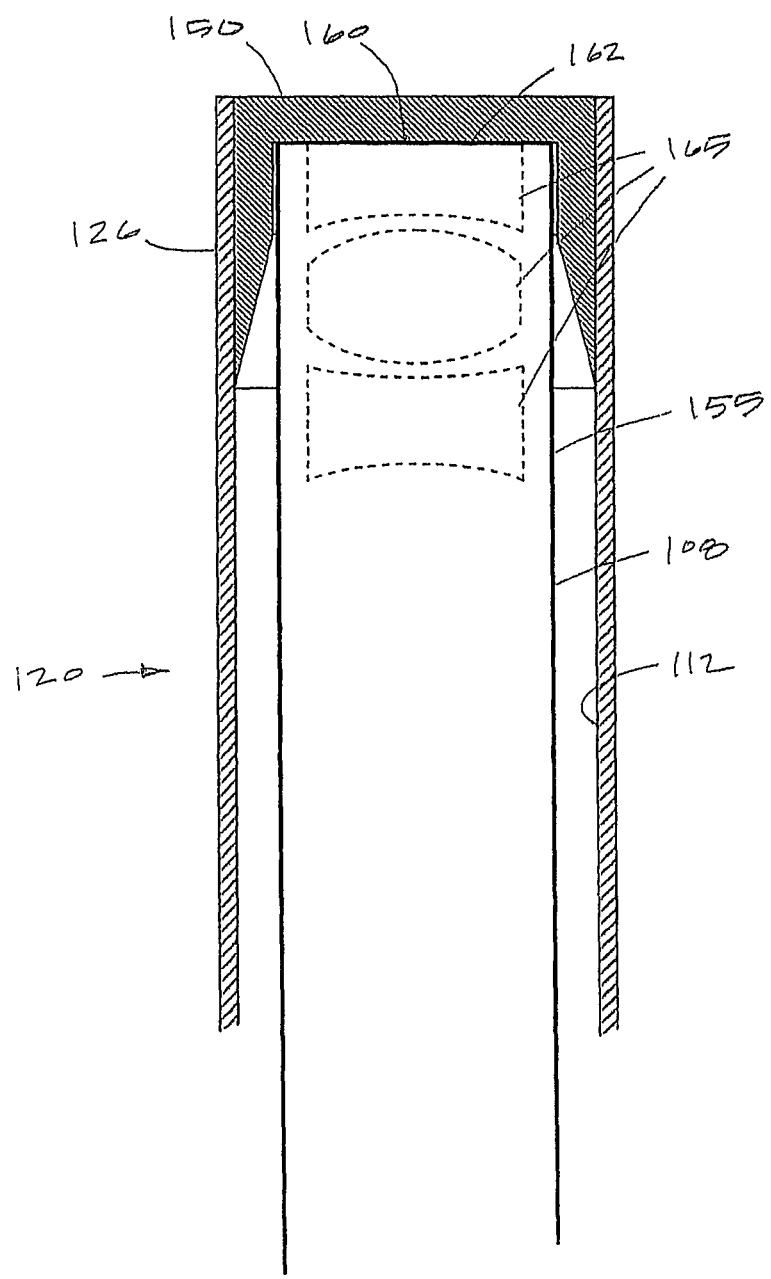
FIG. 3 is an enlarged sectional view of the distal region of the sheath of FIGS. 1 and 2.

It can be understood from FIGS. 1 and 2 that the flexible, elastomeric distal region 120 allows for side-by-side deflection as shown in FIG. 2 in response to the articulation of the distal region 155 of endoscope shaft 108. As can be further understood from FIGS. 2 and 3, the distal region 120 of sheath 100 is adapted to maintain the interior surface 160 of end cap 150 in perfect contact with the distal tip 162 of the endoscope 105 which includes the endoscope lens 165. It is desirable to maintain the interior surface 160 of end cap 150 in contact with the endoscope distal tip 162 and endoscope lens 165 to prevent any reflections or distortions. It is for this reason that the distal region 120 of sheath 100 has axial elasticity which thereby maintains the interior surface 160 of end cap 150 in contact with the endoscope lens 165 no matter whether the endoscope's distal region 155 is in a non-articulated/linear configuration or is articulated to the left or right (or any direction). In order to provide and maintain axial tension between the end cap 150 and the endoscope lens 165, the sheath 100 is initially tensioned over the endoscope 105 when the endoscope is inserted into the channel 112 and thereafter clamping the clamp mechanism 140 over the endoscope shaft 142 as can be understood from FIG. 1. The endoscope shaft 108 can be provided with markings (not shown) to indicate the proper location for locking the sheath 100 to the endoscope shaft 108. In another variation, the sheath 100 and endoscope 105 can be designed for use with one another and the sheath 100 and endoscope 105 can be provided with cooperating first and second features that are adapted to lock the proximal end 142 of the sheath 100 in a predetermined axial location on the endoscope shaft 108 to axially tension the elastomeric distal region 120.

As can be understood from FIGS. 1 and 2, and endoscope 105 can be introduced without friction through the rigid sleeve 126 of the proximal region of sheath 100, and then easily manipulated to slide through the short, flexible distal region 120 of the sheath. It should be appreciated that the interior surface of the channel 112 throughout the length of the sheath 100 can be provided with one or more lubricious coatings to allow for ease of insertion of the endoscope shaft 108.

Figure 4:
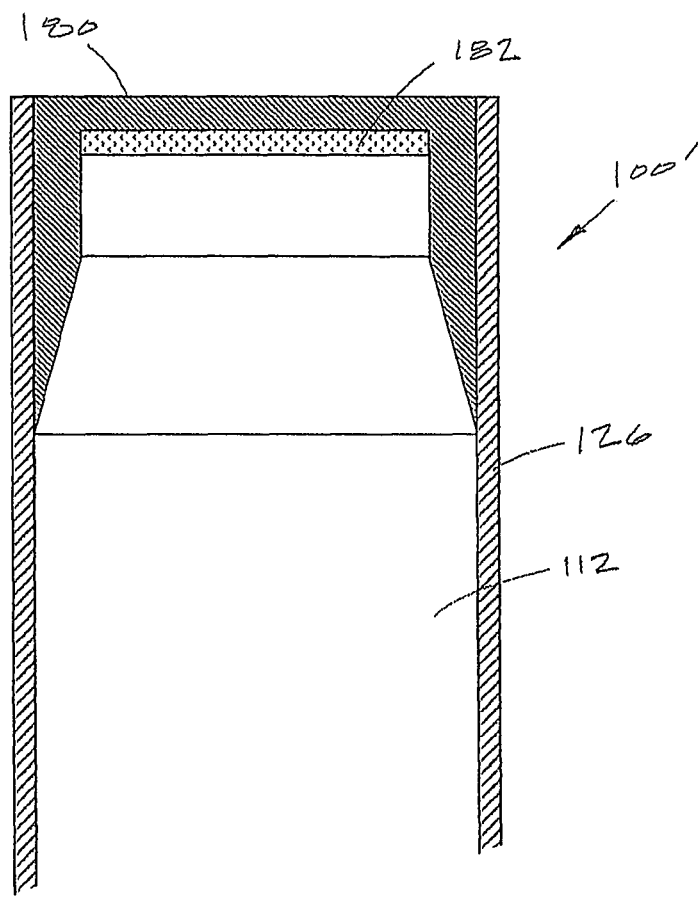
FIG. 4 is an enlarged sectional view of an alternative distal sheath region similar to that of FIG. 3.

Now referring to FIG. 4, another variation of sheath 100' has a distal end cap 180 that includes an interior layer 182 of a transparent resilient material such as a silicone, for example, and index-matched silicone that matched the index of refraction of the end cap 180 and/or any transparent distal endoscope tip. In this variation, the interior layer 182 can have a thickness ranging from 0.05 inches to 0.2 inches or more is adapted to be compressed slightly against the endoscope tip or lens to again insure that there is no reflection in the interface between the end cap 180 and the endoscope lens.

Figure 5:
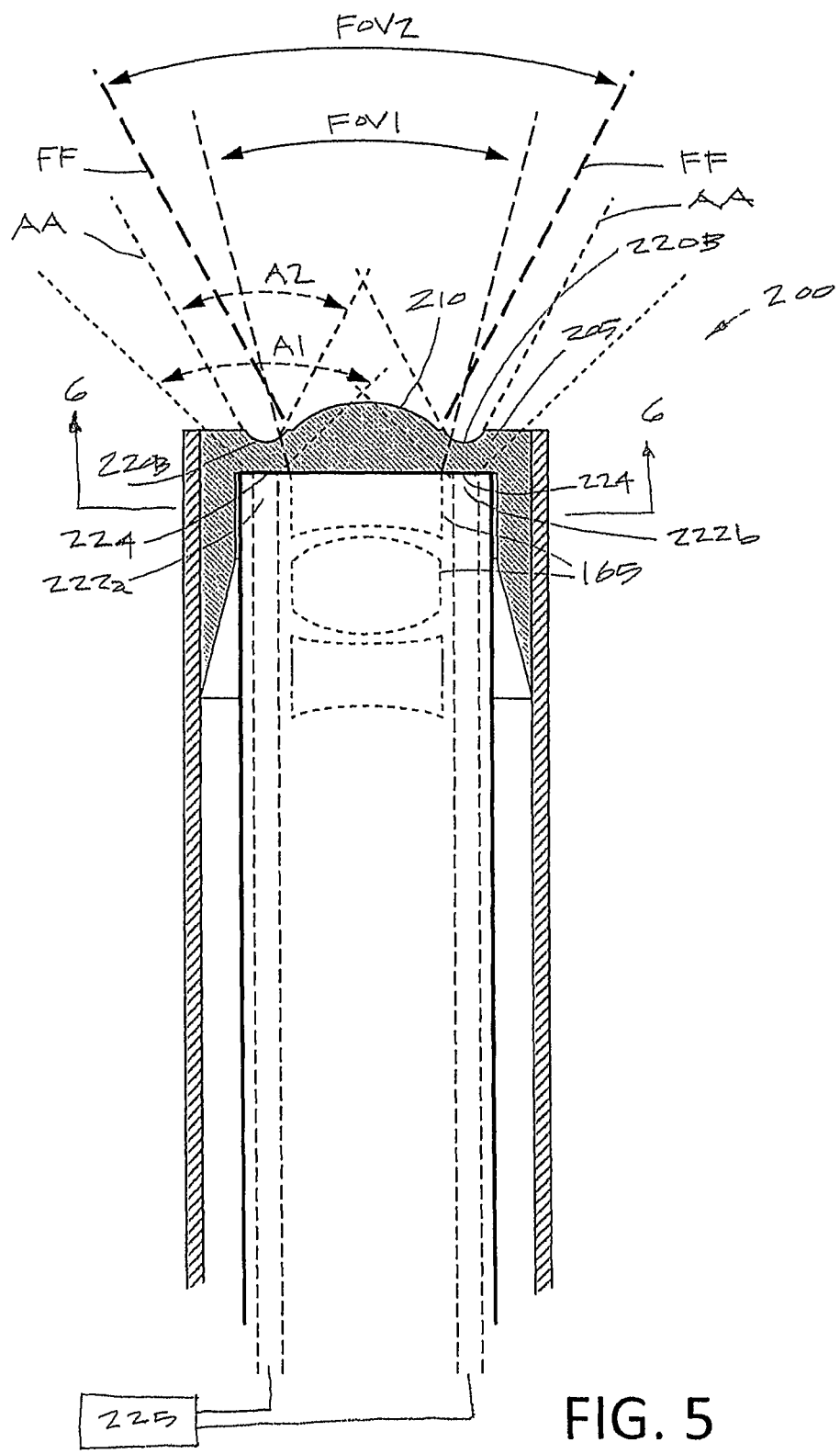
FIG. 5 is a sectional view of another variation of a sheath, and more particularly a distal sheath end cap that includes first and second focusing components for modifying an image sensor's field of view and the angle of illumination of light emitters.

FIG. 5 illustrates another variation of sheath 200 that has an end cap 205 that includes at least one lens or focusing component. In the variation shown in FIG. 5, a first lens 210 is shown and is configured for modifying the field of view provided by endoscope lens 165. For example, the field of view is expanded or broadened from the original endoscope field of view indicated at FOV 1 to the sheath-modified field indicated at FOV2. Often, the endoscope field of view may be overly narrow and the sheath lens 210 thus can provide an enhanced or widened field of view. In another variation, the lens or the lens in combination with a prism can be used to provide an angled and wider field of view.

FIG. 5 further illustrates a second focusing component which comprises a plurality of second lenses 220A and 220B which are configured to modify the angle of illumination of light illumination means carried by the endoscope. In FIG. 5, the endoscope 105 is shown with first and second light channels or emitters 222a and 222b which can comprise optic fibers extending from a light source 225 or can comprise LEDs in the distal end of the endoscope 105. The second lenses 220A and 220B are configured to abut the distal surface 224 of each of the light emitters 222a and 222b to thereby modify the angle of illumination of each of the light emitters. In the variation of FIG. 5, it can be seen that the angle of illumination is narrowed from angle A1 to angle A2 for light emitter 222a.

In one variation, the second lenses 220A and 220B are configured to converge the light angles of illumination A2 with the field of view of the endoscope, or with the modified field of view FOV2 provided by the first lens 210 described above, as indicated schematically in FIG. 5 by light emission angle AA generally converging with field of viewing angle FF.

Figure 6:
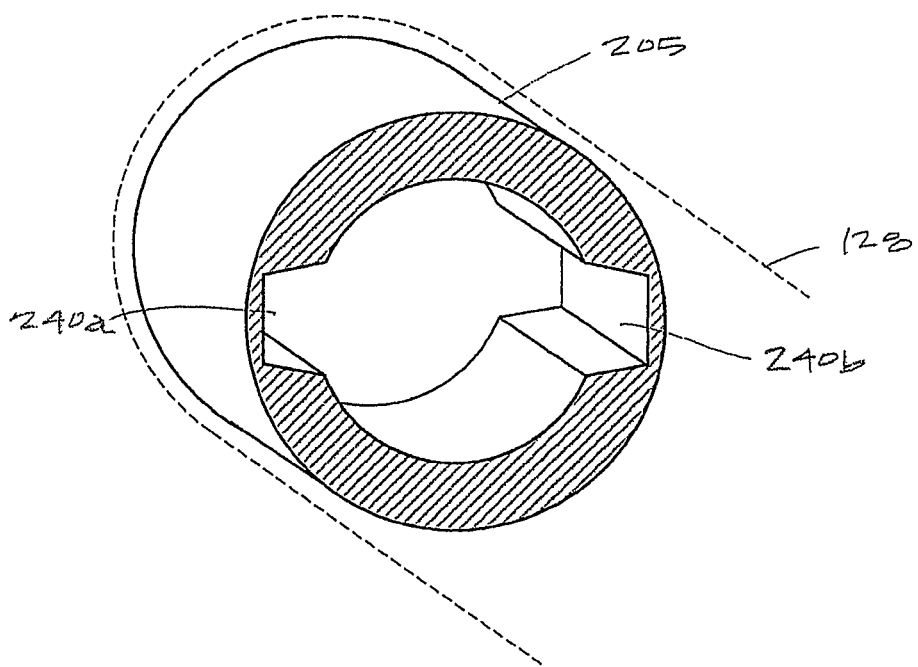
FIG. 6 is a sectional view of a transparent sheath end cap of the type shown in FIG. 5 taken along line 6-6 of FIG. 5 that includes key features for cooperating with an endoscope to align focusing components with an endoscope's image sensor and/or light emitters.
Figure 7:
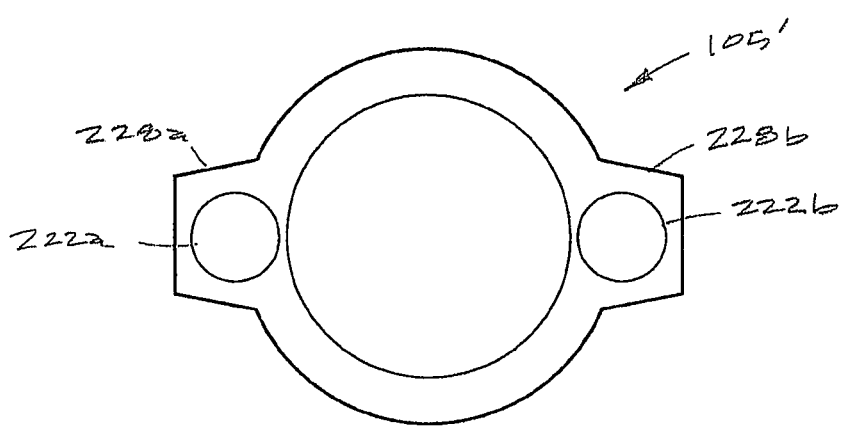
FIG. 7 is an end view of an endoscope with key features adapted to cooperate with a sheath endcap as shown in FIG. 6.

Now turning to FIG. 6, one variation of end cap 205 of the type shown in FIG. 5 has a non-round interior channel shape, for example, with key features to ensure that the first and second focusing components, that is, lenses 210, 220A and 220B of FIG. 5, are properly aligned with the endoscope lens 165 and the light emitters 222a and 222b when the sheath 200 and endoscope 105 are assembled together. FIG. 7 shows an end view profile of the distal end of a custom endoscope 105' which has a non-round shape with protruding portions 228a and 228b that carry the light channels or emitters 222a and 222b. In FIG. 6, it can be seen that the end cap 205 has side channel portions 240a and 240b adapted to receive the protruding portions 228a and 228b of the endoscope of FIG. 7 which will thereby insures alignment and registration of the first and second focusing components with the endoscope lens 165 and the light emitters 222a and 222b.

Figure 8:
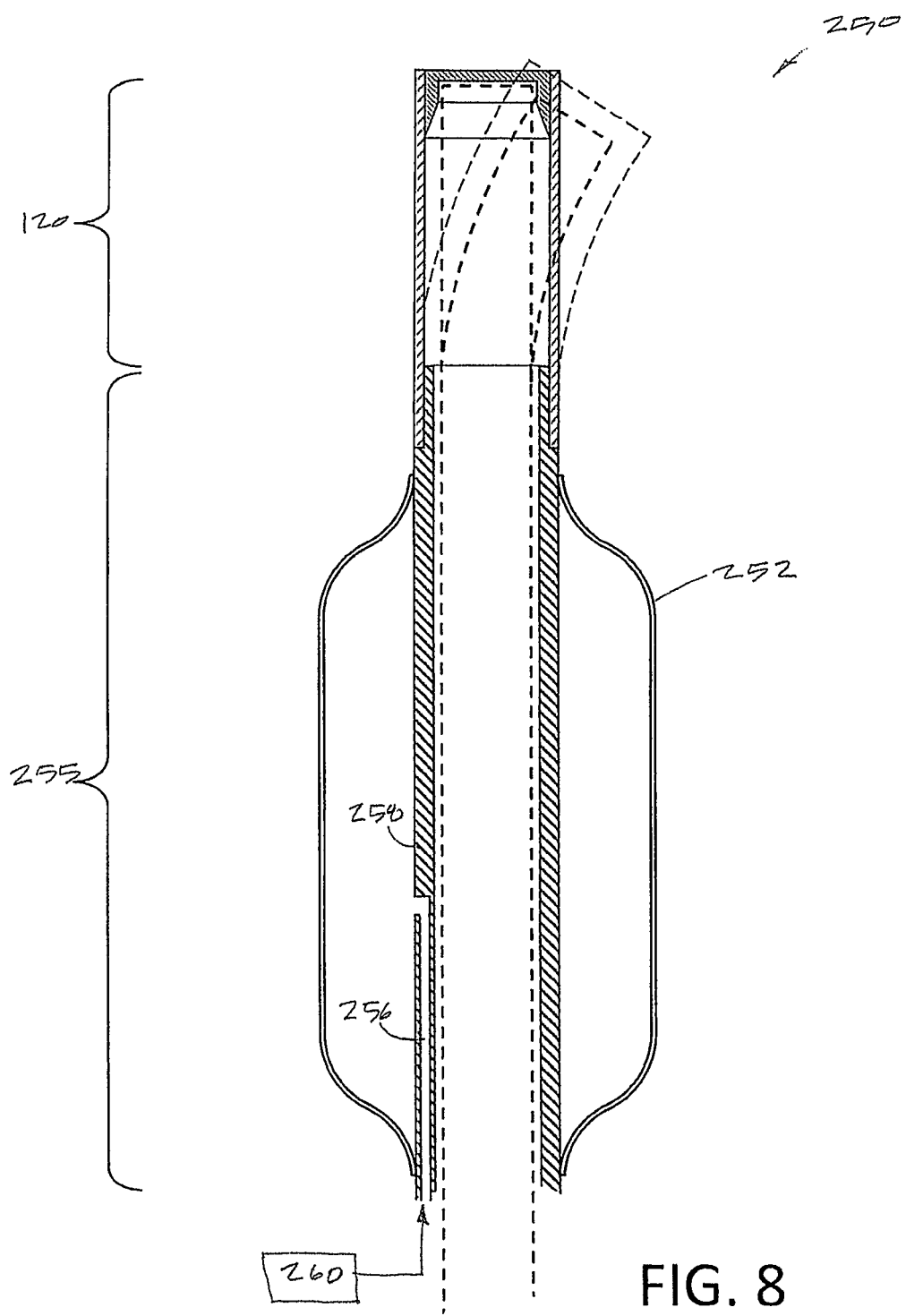
FIG. 8 is a sectional end view of the medial and distal regions of an alternative sheath similar to that of FIG. 3, with this variation carrying an expandable balloon for use in sealing an access pathway in a patient's body, for example, and endocervical canal.
Figure 9:
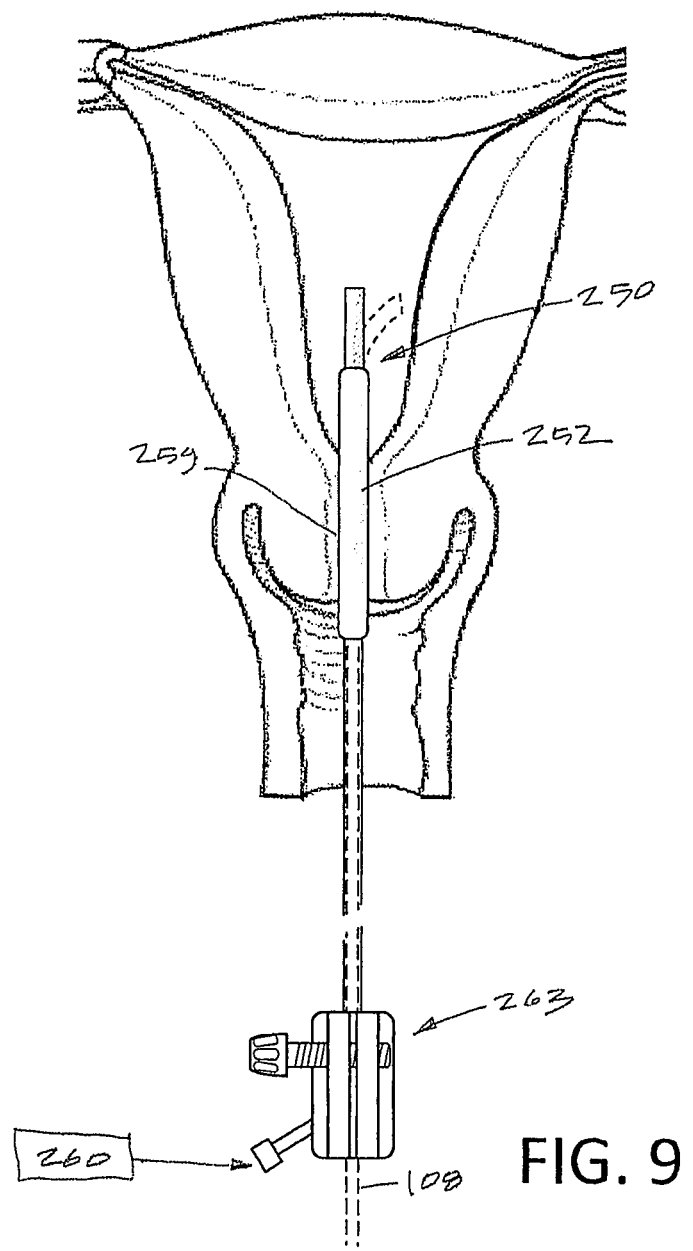
FIG. 9 is a schematic view of the alternative sheath of FIG. 8 with the balloon used to seal an endocervical canal and an articulating endoscope in phantom view.

FIGS. 8 and 9 illustrate another variation of sheath 250 that is similar to the embodiments described above except that sheath 250 carries an expandable balloon 252 in or about a medial portion 255 of the sheath and further has a balloon inflation channel or lumen 256 in the wall 258 of the sheath 250. An inflation source 260 such as a syringe can be used to inflate the balloon 252. In this variation, the sheath 250 can be adapted for trans-cervical access to a woman's uterus as shown in FIG. 9 and the expandable balloon 252 can be expanded in the endocervical canal 259 as a seal to confine irrigation fluids to the uterine cavity as is known in the art.

Figure 10:
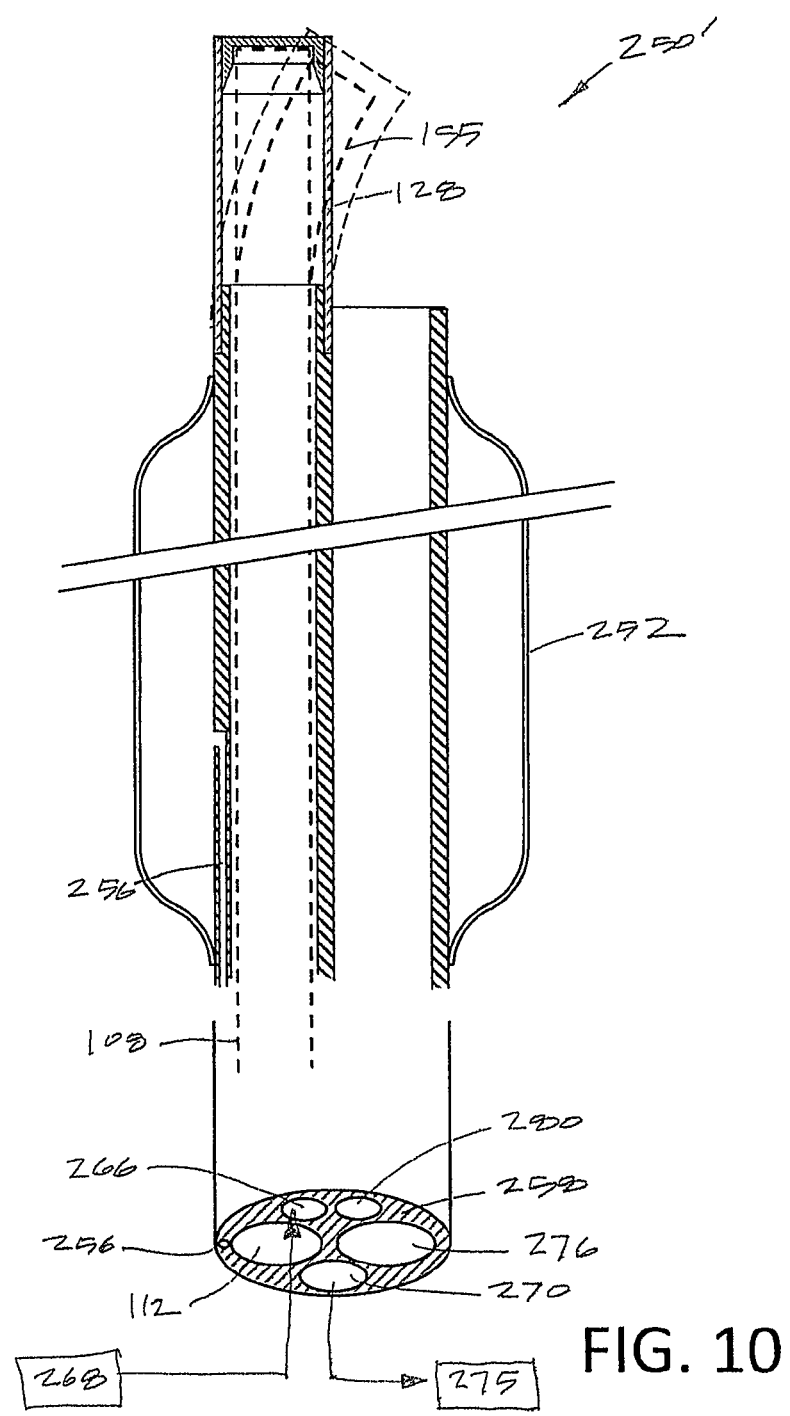
FIG. 10 is a cut-away view of another variation of an endoscope sheath similar to that of FIG. 8, wherein the sheath is configured with additional channels for use in cooperation with a fluid management system, for example such channels use for fluid inflows, fluid outflows, working channels for tool introduction, and for pressure sensing.

The variation of FIG. 10, the wall 258 of sheath 250' further is configured with additional channels that extend from a proximal handle portion 263 (see FIG. 8) of the sheath to an open termination in a distal portion of the sheath. In the variation of FIG. 10, a fluid inflow channel 266 is provided for coupling to a fluid source 268 to deliver an inflow of an irrigation fluid to the body cavity, for example a patient's uterine cavity as in FIG. 9. In this variation, a fluid outflow channel 270 can be provided for coupling to a negative pressure source 275 thereby providing fluid outflows from the patient's body cavity. In a variation, a working channel 276 as shown in FIG. 8 can be provided for the introduction of a diagnostic or therapeutic instrument into the patient's body cavity. In this variation, an instrument seal or flap valve (not shown) as is known in the art can be provided in a proximal end of the working channel. In a variation, shown in FIG. 10, another channel 280 can be provided to function as a pressure sensing channel wherein a pressure sensor mechanism can be coupled to the proximal end of the open channel 280 in a handle of the sheath.

Figure 11:
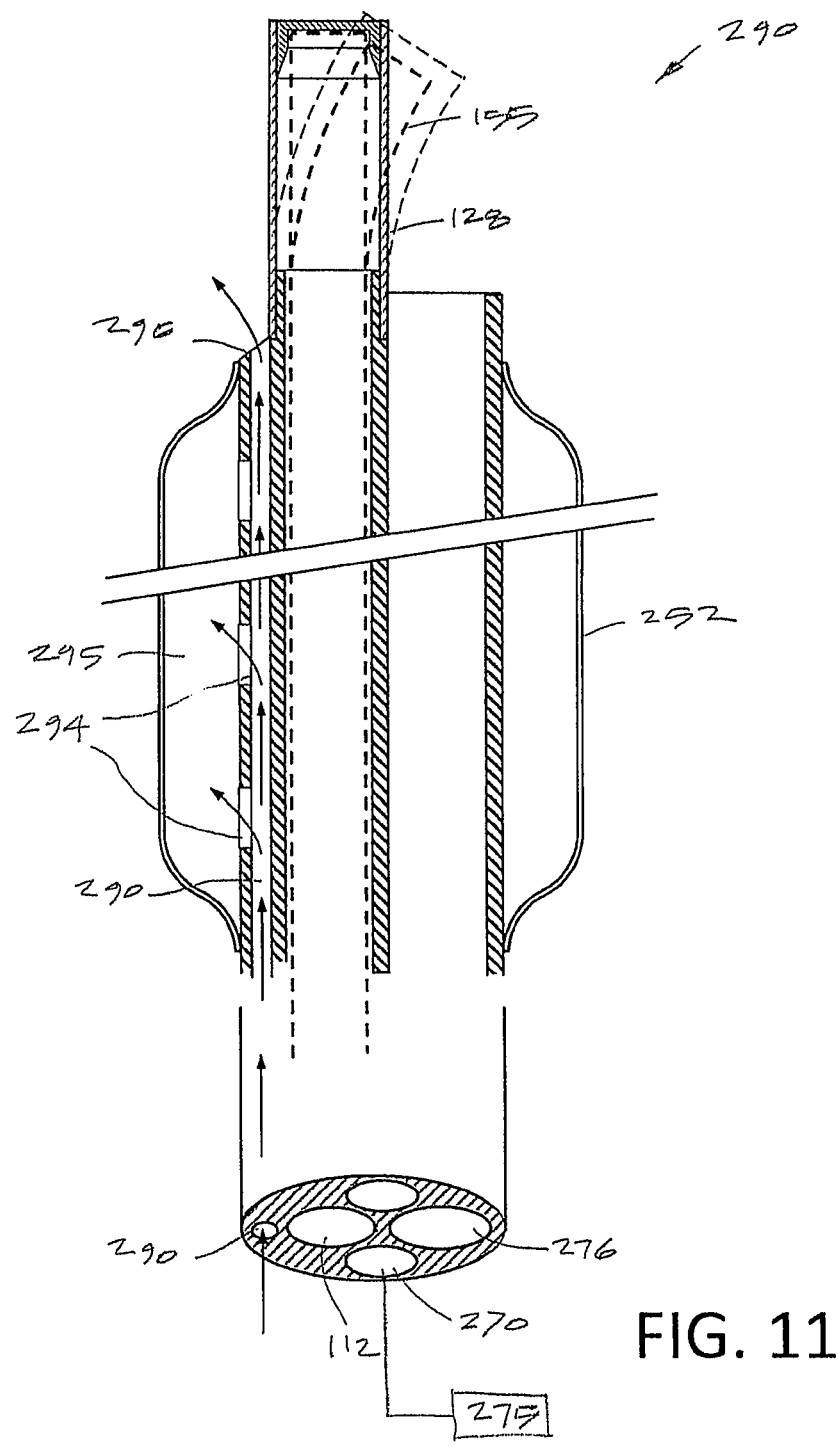
FIG. 11 is a cut-away view of another variation of endoscope sheath similar to FIG. 10 wherein the sheath is configured with a single channel that functions as a balloon inflation channel and a fluid inflow channel.

In another variation shown in FIG. 11, the sheath 290 can be configured for trans-cervical access to a patient's uterine cavity as described above, and a single fluid inflow channel 290 can be used for two functions. First, the inflow channel 290 can have a ports 294 that open to the interior chamber 295 of the sealing balloon 252 to expand the balloon as described above. Second, the inflow channel 290 can also extend to an open end 296 in a distal region of the sheath 290 to provide a fluid inflow of irrigation fluid to the uterine cavity to thereby expand the cavity. In this variation, the pressure of the fluid inflow is adapted to perform both the function of expanding the balloon 252 and simultaneously providing a suitable rate of fluid flow into and through the uterine cavity to expand the cavity in combination with the outflow channel 270 as described previously.

FIG. 12A is a cut-away view of another variation of a device similar to those described above, except that the device of FIG. 12A comprises a separate introducer 300 that carries the sealing balloon 302 and multiple inflow, outflow and access channels. In this variation, the introducer 300 has an interior channel 305 adapted to receive the independent endoscope sheath 100 (and endoscope 105) of FIG. 1. Further, the introducer 300 of FIG. 12A has a multifunctional fluid inflow channel 310 for expanding the sealing balloon 302 and for providing a fluid inflow into a body cavity as described in the embodiment of FIG. 11. This variation includes a check valve 312 that opens at a selected pressure to provide the irrigation inflows, wherein the check valve opens at a pressure that insures that the sealing balloon 302 is already expanded.

Figure 12A:
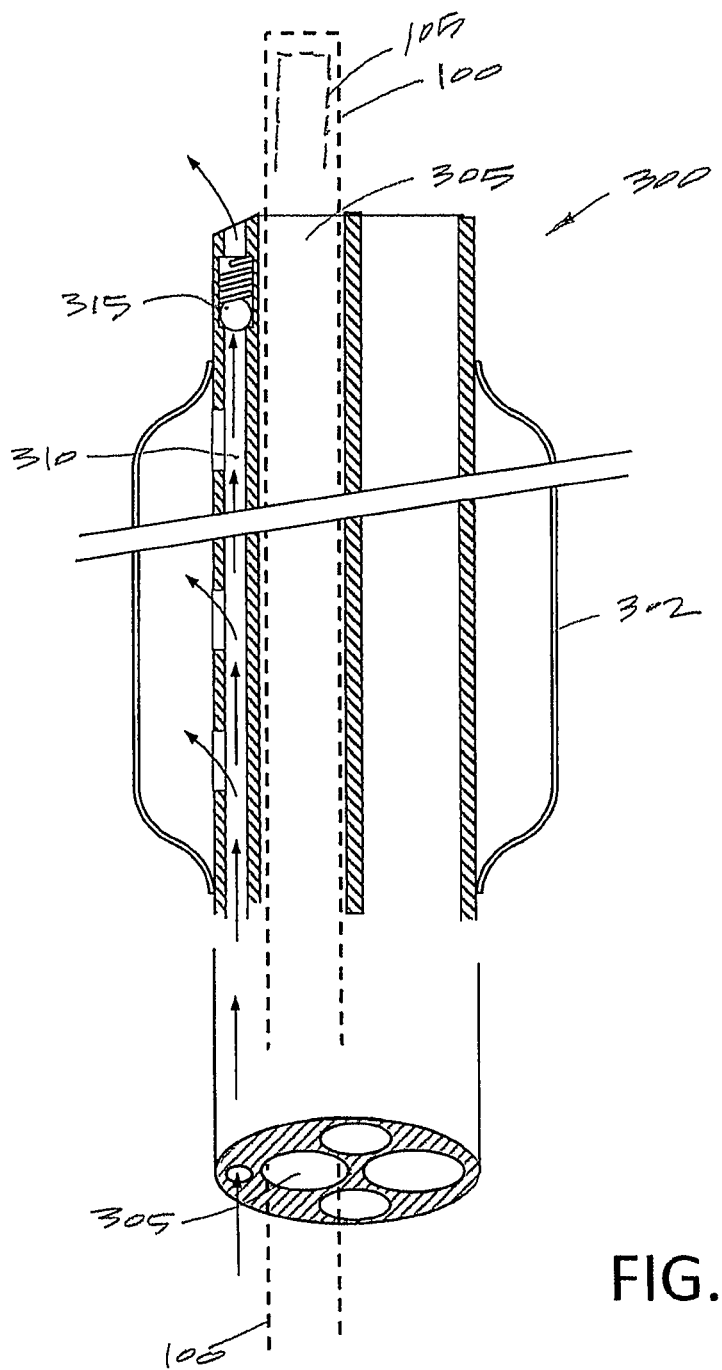
FIG. 12A is a cut-away view of another variation of a device similar to those described above, except that the device of FIG. 12A comprises a separate introducer that carries the sealing balloon and multiple inflow, outflow and access channels, and has an interior channel adapted to receive the independent endoscope sheath (and endoscope) of FIG. 1, and wherein the multi-functional fluid inflow channel for expanding the sealing balloon includes a check valve that opens at a selected pressure to provide a fluid inflow into a body cavity.
Figure 12B:
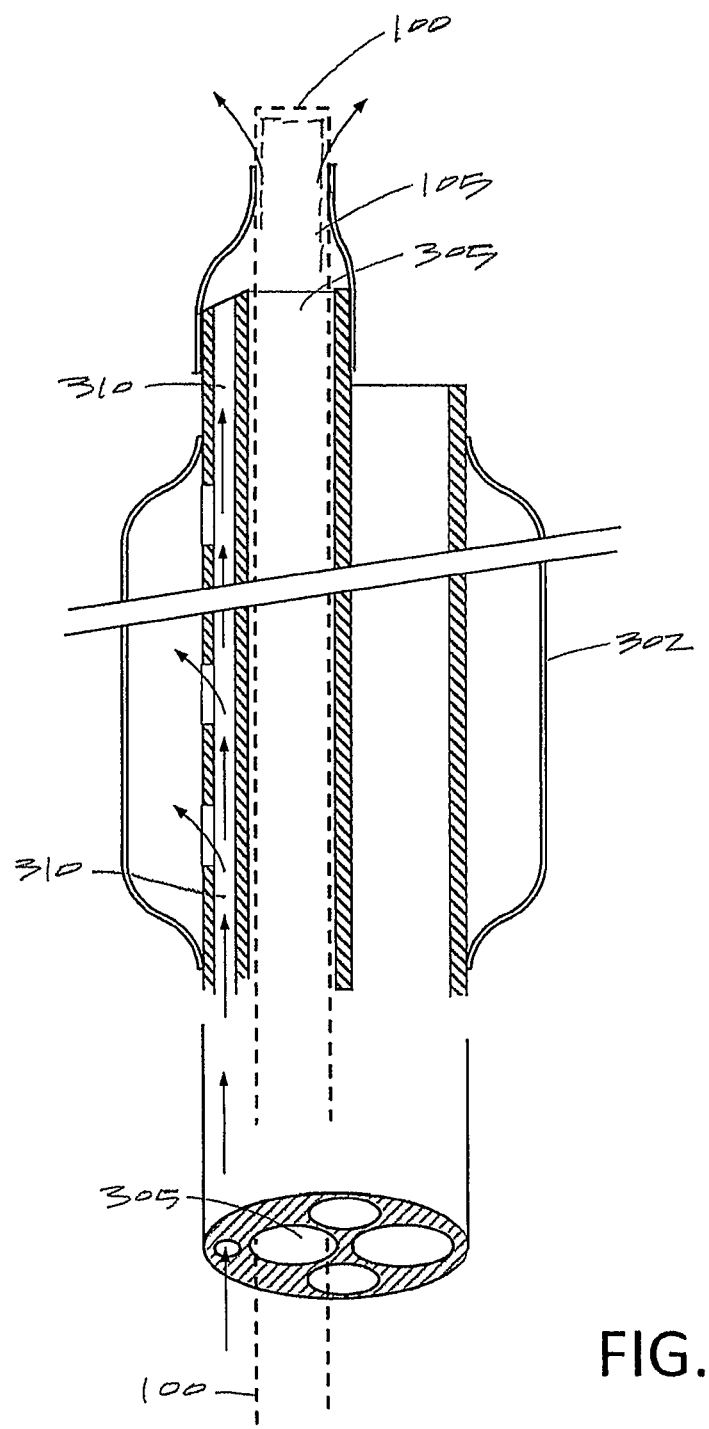
FIG. 12B is a cut-away view of another variation of an introducer device similar to that of FIG. 12A wherein the multi-functional fluid inflow channel for expanding the sealing balloon and providing irrigation flows has an elastomeric skirt that functions as a check valve and opens at a selected pressure to provide a fluid irrigation or inflow into a body cavity.

FIG. 12B is a cut-away view of another variation of an introducer 300' that is similar in function to introducer 300 of FIG. 12A wherein the multi-functional fluid inflow channel 305 for expanding the sealing balloon 302 and for providing irrigation flows has an elastomeric skirt 320 that functions as a check valve and opens at a selected pressure to provide a fluid irrigation or inflow into a body cavity. in FIG. 12B, it can be seen that the skirt 320 is resiliently closed against the sheath 100 but can release fluid under pressure. In another variation, the skirt 320 can comprise a duck-bill valve as is known in the art for closing in the absence of a tool (or sheath 100) introduced therethrough.

As described above in one aspect of the invention, the sheaths (or endoscopes themselves) can carry focusing components for modifying the field of view of the image sensor. In general, what is needed is a endoscopic system that provides for broader fields of view than can be provided by current state of the art sensors.

An alternative means of expanding an endoscope's field of view is to use a plurality of image sensors. In one variation known in prior art endoscopes, two or more image sensors are used an a display simply shows multiple non-overlapping images next to one another.

In one embodiment, the distal end of the endoscope carries a plurality of image sensors which are configured to expand the field of view provided by the endoscope. Each image sensor, which for example is a CMOS chip, is coupled through a series of the electrical leads to a processing module in a handle of the endoscope, or the electrical leads may be coupled by wires or wirelessly to a remote component for image processing.

FIGS. 13A and 13B illustrate an endoscope 500 with two image sensors 505A 505B comprising CMOS chips carried at the distal end 506 of an endoscope shaft 508. The fields of view FOV1 and FOV2 overlap.

As can be seen in FIGS. 13A and 13B, the distal end 510 of the endoscope carries light emitters such as LEDs indicated at 512*a* and 512*b*. A cover class 514 is bonded to sleeve 518 that comprises the end of the endoscope shaft. Each of the image sensors has electrical leads 522*a* and 522*b* that extend to an image processing module 525 that may be in the endoscope handle or can be where connected by a cable or wirelessly to a remote module. The number of leads may vary from 2 to 16 or more per image sensor but typically may be four leads. The LEDs 512*a* and 512*b* also have electrical cables 534 extending to an electrical source 535. The sectional profile of the endoscope distal end 510 can have a sectional profile similar to that described previously (see FIGS. 6-7) with keys 536*a* and 536*b* for cooperating with a sterile disposable sheath as described above.

In one aspect of the invention, the system of FIGS. 13A-13B can include image processing software in the processing module 525 that can seamlessly "knit" the edges of the overlapping images together to provide a seamless, expanded field of view indicated at FOV3.

Figure 14:
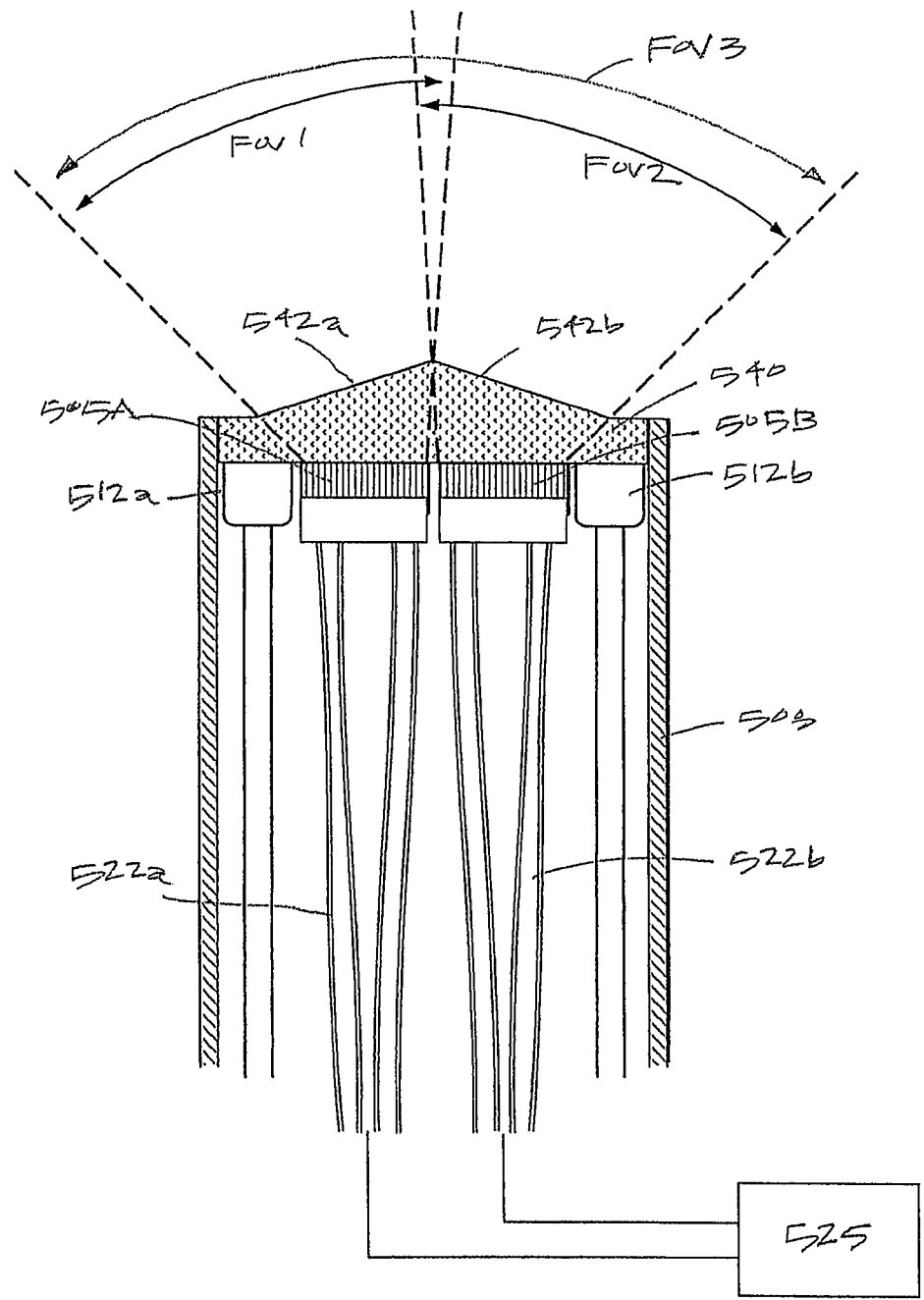
FIG. 14 is a longitudinal sectional view of a variation of an endoscope distal end with prisms for modifying the fields of view of two imaging sensors.

Now turning to FIG. 14, an endoscope similar to that of FIGS. 13A-13B is shown except that a distal cover glass or tip 540 includes prism or lens portions 542*a* and 542*b* which are adapted to modify the field of view to FOV3. In this variation, it can be seen that the image overlap is greatly reduced.

Figure 15:
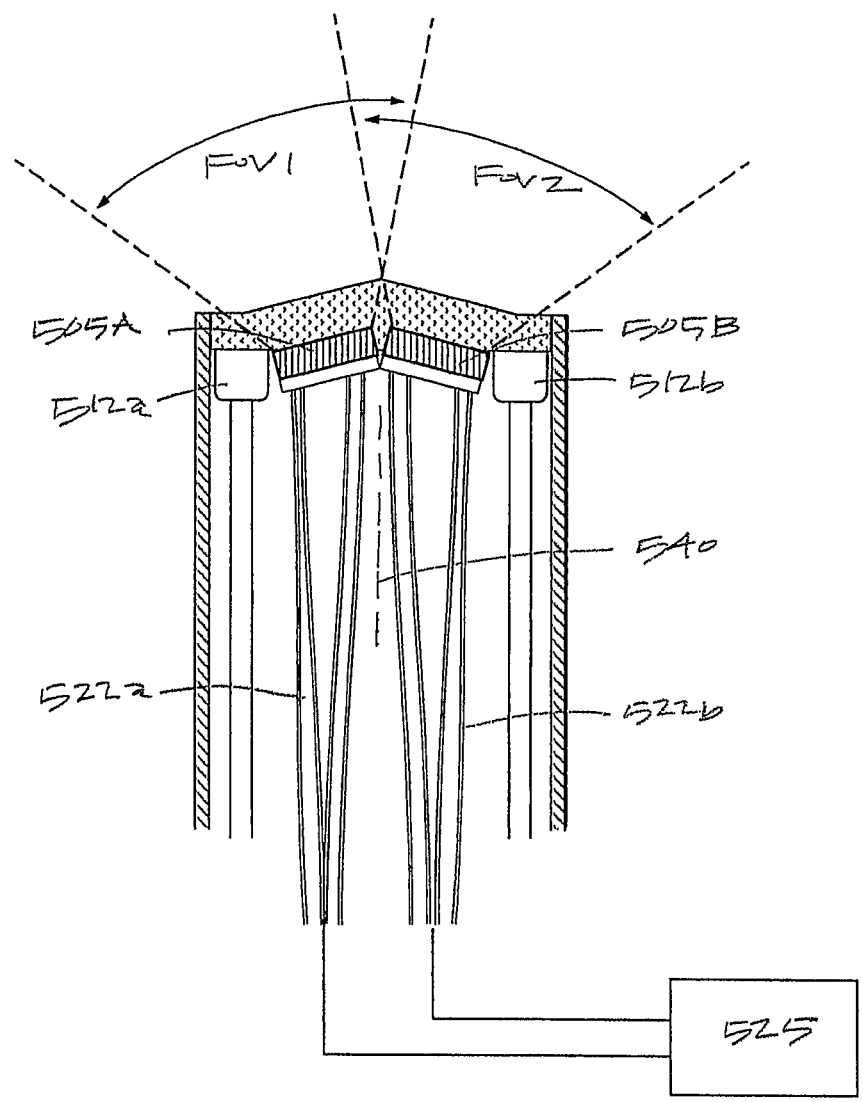
FIG. 15 is a longitudinal sectional view of a variation of an endoscope distal end with two imaging sensors positioned as angles for increasing an expanded, knit-together field of view.

FIG. 15 illustrates another embodiment that is similar to that of FIG. 14 except that the images sensors 505A and 505B themselves are angled relative to the axis 540 of the endoscope to create an increase field of view FOV3 when knit together. As described above, software algorithms can be used to knit together the overlap of the field of views to provide a single seamless image.

Figure 16:
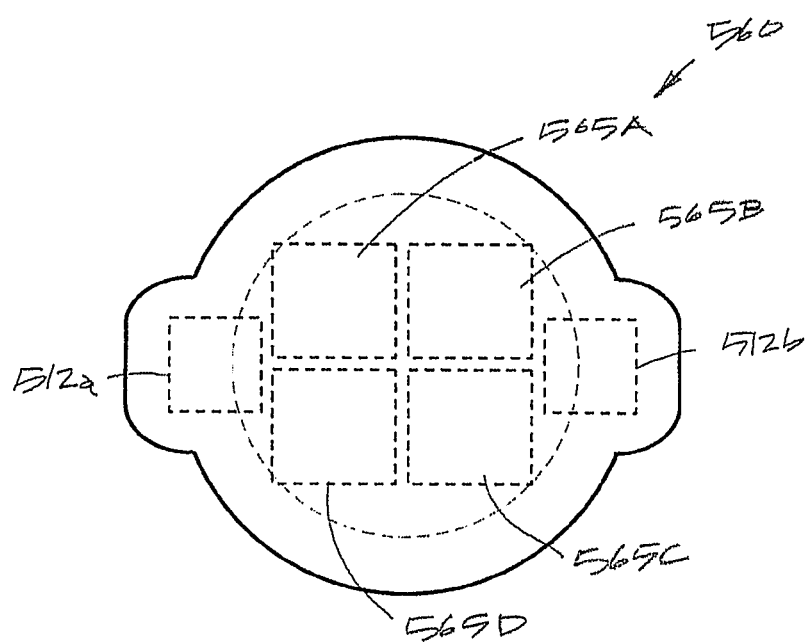
FIG. 16 is an end view of the distal end of an endoscope with four imaging sensors.
Figure 17:
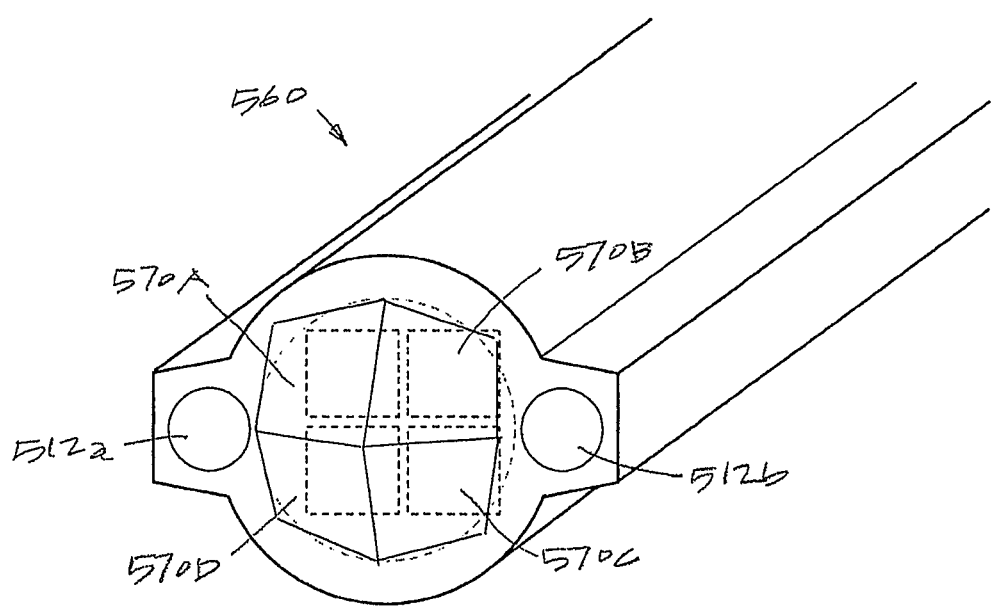
FIG. 17 is a longitudinal sectional view of the endoscope distal end of FIG. 16 showing four prisms for modifying each sensor's field of view.

FIGS. 16 and 17 illustrate another endoscope distal end 560 with four sensors 565A-565D and LEDs 512*a* and 512*b*. FIG. 17 illustrates 4 prisms 570A-570D or facets for oriented each sensors field of view similar to that of FIG. 14. In this variation, the image processor is capable of processing the images taken with each image sensor and can knit together the image data in the overlapping portions of the fields of view to thereby create a broad seamless combined field of view.

The software algorithms for knitting together the data from multiple image sensors has been developed can be acquired from and/or developed by Helion GmbH, Tec-Tower, Bismarckstrasse 142, 47057 Duisburg-Neudorf, Germany (see www.HelionVision.com). Similar software systems may be available or can be developed by Honeywell and is related to their software known as a MaxPro VMS system.

The software algorithms for knitting together the data from multiple images has been developed by Honeywell and is known as a MaxPro VMS system.

In alternate embodiments, there may a single channel for inflating and expanding a plurality of balloon carried by a sheath, or there may be inflation channels thereby allowing separate and/or different inflation of the separate balloons. Such separate balloons may be inflated to different sizes, for example in the cervical canal and interior of the internal os. Alternatively, a balloon may have more than one compartment which can be inflated individually or all compartments can be inflated at the same time.

The balloons may be arranged in many configurations on the sleeve, including but not limited to being arranged longitudinally as described above. Alternately, one or more balloons may be arranged to form a spiral or helical ridge. The balloons may be fixed or moveable. The balloons and inflation/deflation lumens may be.

The expandable balloons may be fabricated an suitable compliant, non-compliant, or combination of materials. For examples, compliant materials include but are not limited to silicone, polyethylene, polyurethane; Tecoflex®, or the like. Examples of non-compliant materials include nylon, polyester, Pebax®, polyimide or a combination of such materials.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein

What is claimed is:

1. A disposable cover for use with an endoscope, comprising:
    an elongated sheath having an open proximal end, a closed distal end, and a central axis therebetween;
    a channel extending from the open proximal end to the closed distal end, the channel being configured to accommodate insertion of the endoscope;
    wherein a proximal region of the elongated sheath comprises a rigid thin-wall metal sleeve and a distal region of the sheath comprises a flexible thin-wall elastomeric sleeve configured to allow deflection of said distal region in cooperation with an articulating distal end of the endoscope wherein the proximal region of the sheath includes a lock mechanism for locking said proximal region to a shaft of the endoscope.

2. The disposable cover of claim 1 wherein the flexible thin-wall sleeve of said distal region is configured to allow a side-to-side deflection.

3. The disposable cover of claim 2 wherein the flexible thin-wall sleeve of said distal region is stretchable in an axial direction.

4. The disposable cover of claim 1 wherein the lock mechanism comprises a clamp mechanism.

5. The disposable cover of claim 1 wherein the lock mechanism includes cooperating first and second engagement features on the sheath and endoscope respectively.

6. The disposable cover of claim 1 wherein the closed distal end of the distal region of the sheath comprises at least one lens.

7. The disposable cover of claim 1 wherein the closed distal tip of the distal region of the sheath includes a lens adapted to modify a field of view of the endoscope.

8. The disposable cover of claim 1 wherein the closed distal tip of the distal region of the sheath includes a lens adapted modify the angle of illumination of a light emitter in the endoscope.

9. The disposable cover of claim 1 further comprising a channel in a wall of the sheath extending from a pressure sensor mechanism at a proximal channel end and an open distal channel end for measuring pressure in the interior of a patient's body.

10. The disposable cover of claim 1 further comprising a channel in a wall of the sheath communicating with an inflatable balloon carried by a medial region of the sheath, wherein the sheath has at least a first key feature which cooperates with a second mating key feature on the endoscope to thereby maintain the distal region of the sheath in a predetermined rotational position relative to the endoscope.

11. The disposable cover of claim 10 wherein the first key feature is disposed in the distal region of sheath and is configured to engage a shape of a distal end of the endoscope.

12. The disposable cover of claim 11 wherein the first key feature is disposed in the proximal region of sheath and is configured to engage the second mating key feature in a proximal portion of the endoscope.

13. The disposable cover of claim 1 wherein the closed distal tip of the distal region of the sheath has an interior surface of a resilient material for interfacing with the distal surface of the endoscope.

14. The disposable cover of claim 1 further comprising an inflation channel in a wall of the sheath communicating with an inflatable balloon carried by a medial region of the sheath.

15. The disposable cover of claim 14, wherein the inflatable balloon is carried by a medial region of the sheath and further wherein the distal portion of the sheath comprises an open end for providing a fluid inflow to the interior of a patient's body.

16. The disposable cover of claim 1 further comprising an inflow channel in a wall of the elongated sheath, wherein the inflow channel is adapted for coupling to a fluid source for providing a fluid inflow to the interior of a patient's body.

17. The disposable cover of claim 1 further comprising an outflow channel in a wall of the elongated sheath adapted for coupling to a negative pressure source for providing fluid outflow from the interior of a patient's body.

18. The disposable cover of claim 1 further comprising at least one working channel in a wall of the sheath extending from an open proximal end to an open distal end for introducing a medical device therethrough.

* * * * *